United States Patent [19]

Fenton, Jr. et al.

[11] Patent Number: 4,769,010
[45] Date of Patent: Sep. 6, 1988

[54] CATHETER NEEDLE ASSEMBLY WITH ADJUSTABLE HEIGHT SUPPORT

[75] Inventors: Paul V. Fenton, Jr., Marblehead; Thomas M. Young, North Andover, both of Mass.

[73] Assignee: Strato Medical Corporation, Beverly, Mass.

[21] Appl. No.: 13,322

[22] Filed: Feb. 11, 1987

[51] Int. Cl.⁴ .............................................. A61M 25/02
[52] U.S. Cl. ............................. 604/180; 128/DIG. 26
[58] Field of Search ............... 604/177, 174, 180, 117; 128/DIG. 26

[56] References Cited

U.S. PATENT DOCUMENTS

| | | | |
|---|---|---|---|
| 3,288,137 | 11/1966 | Lund | 604/180 X |
| 3,368,564 | 2/1968 | Selix | 128/DIG. 26 |
| 4,235,234 | 11/1980 | Whitney et al. | 604/177 |
| 4,392,854 | 7/1983 | Tback | 128/DIG. 26 |
| 4,606,735 | 8/1986 | Wilder et al. | 128/DIG. 26 X |
| 4,626,246 | 12/1986 | Verkade | 128/DIG. 26 X |

Primary Examiner—Stephen C. Pellegrino
Attorney, Agent, or Firm—Lahive & Cockfield

[57] ABSTRACT

The present invention is a catheter needle and support assembly. That assembly includes a hollow bore catheter needle and a needle support assembly. The needle has a proximal port and a distal port an extends along a central needle axis between these port. A distal portion of the needle includes the distal port and extends along a first portion of the needle axis. A support portion extends along a substantially linear second portion of the needle axis between the first portion and the proximal port. The needle axis at the distal port is angularly offset from the second portion of the needle axis. The needle support assembly includes a coupling member and a pair of support members. The coupling member couples the needle support assembly to the support portion of the needle. The pair of support members extend from the coupling member. Each of the support members has a first flexible sheet portion extending form the coupling member and coupled to a second flexible sheet portion by a linear hinge portion extending along a hinge axis displaced from the coupling member.

16 Claims, 4 Drawing Sheets

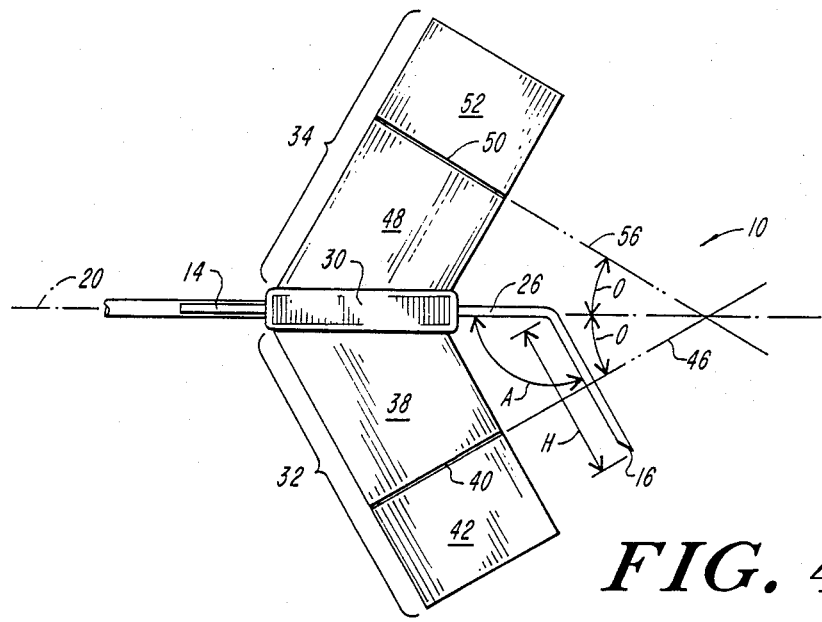
FIG. 4
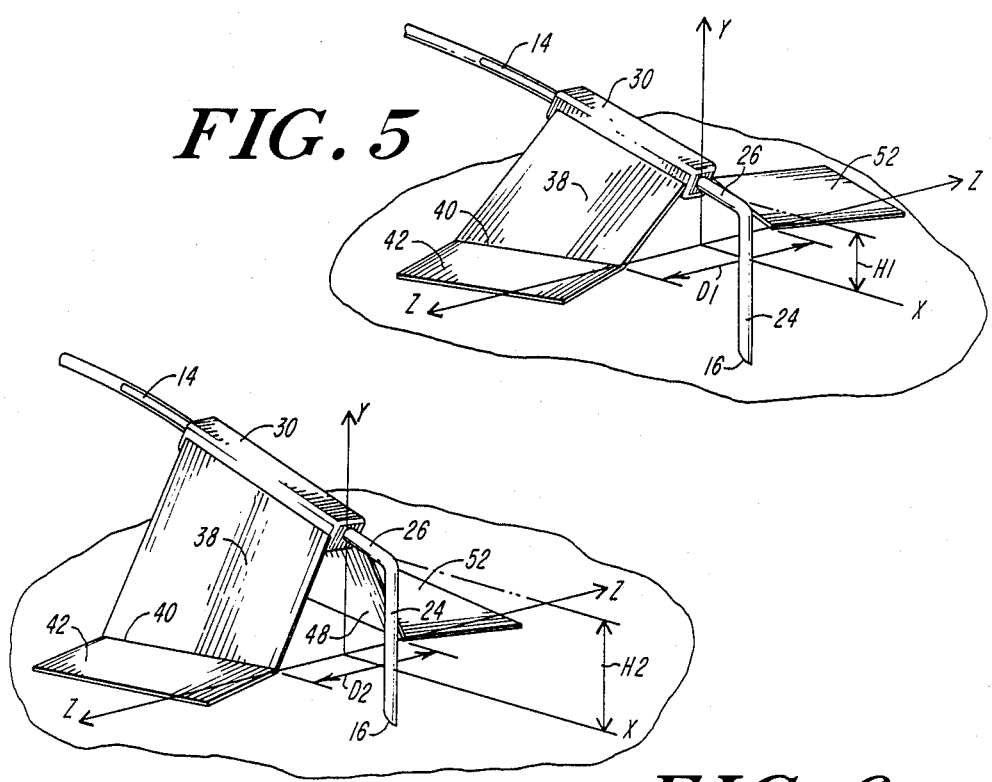
FIG. 5
FIG. 6

CATHETER NEEDLE ASSEMBLY WITH ADJUSTABLE HEIGHT SUPPORT

BACKGROUND OF THE DISCLOSURE

The present invention is in the field of medical devices and more particularly relates to catheter assemblies and supports therefor.

In the prior art, devices for introducing fluids to, or removing fluids from, the body over an extended time period typically have the form of a catheter assembly including a hollow bore catheter needle extending from a flexible tube along a substantially linear central axis. In order to provide continuous access to a near-surface vein, for example, it is common practice to insert the distal tip of such a catheter needle so that the needle's port at that tip is in the desired position within the vein, and the opposite end of the needle extends outside the body of the patient. That outside end may be taped to the patient's skin so that the needle tip is held in position while permitting the patient some freedom of movement. This configuration generally provides the desired continuous access with a relatively low level of discomfort to the patient.

There are known devices which adapt a catheter needle for rapid and efficient placement and fixture to the patient. More particularly, such needles include a hollow bore needle and a needle support assembly. The needle extends along a substantially linear central axis. The needle support assembly includes a coupling member adapted to couple the support assembly to the needle, and a pair of flexible sheet portions extending from that coupling member in wing-like positions. To use this needle assembly, the needle's distal tip is placed in the desired subcutaneous position and then the flexible sheet portions, or wings, are affixed (for example, with adhesive tape) to the skin of the patient to hold the needle in place. By way of example, such devices do permit rapid and efficient fixture to a patient. However, these devices, as well as the earlier described prior devices, do cause discomfort to the patient due to the necessary depression of skin at one side of the point of entry due to the linear form of the needle. Moreover, such devices are generally adapted only for insertion in to near-surface regions of a patient, and cannot be used to permit use with subcutaneous access ports, such as those disclosed in U.S. patent application Ser. No. 820,714, because they do not permit placement of the tip at a depth controlled to accommodate the position of the access port.

Accordingly, it is an object of the present invention to provide an improved catheter needle assembly.

It is another object to provide a catheter needle assembly which produces minimal patient discomfort.

Yet another object is to provide a catheter needle assembly which may be utilized with a controlled depth of its distal tip.

SUMMARY OF THE INVENTION

The present invention is a catheter needle and support assembly. That assembly includes a hollow bore catheter needle and a needle support assembly. The needle has a proximal port and a distal port and extends along a central needle axis between those ports A distal portion of the needle includes the distal port and extends along a first portion of the needle axis. A support portion extends along a substantially linear second portion of the needle axis between the first portion and the proximal port. The needle axis at the distal port is angularly offset from the second portion of the needle axis.

The needle support assembly includes a coupling member and a pair of support members. The coupling member couples the needle support assembly to the support portion of the needle. The pair of support members extend from the coupling member. Each of the support members has a first sheet portion extending from the coupling member and coupled to a second sheet portion by a linear hinge portion extending along a hinge axis displaced from the coupling member.

With this configuration, the so-called second sheet portions may be affixed to the skin of a patient with the hinge axes spaced apart by a specific distance so that the so-called first sheet portions form a tent-like support for the needle. The particular spacing of the hinge axes determines the height of the support portion of the needle, as well as the corresponding depth of penetration of the distal tip. The needle axes and relative orientations of the hinge axes may be determined to accommodate a large variety of uses, including varied entry angle of the needle, as well as varied height, corresponding to depth of penetration of the needle. Moreover, the resultant needle configuration is highly stable and provides a minimum of discomfort to the patient.

BRIEF DESCRIPTION OF DRAWING

The foregoing and other objects of this invention, the various features thereof, as well as the invention itself, may be more fully understood from the following description, when read together with the accompanying drawings in which:

FIG. 4 shows a top view of an alternative embodiment of the catheter needle assembly of the present invention;

FIGS. 5 and 6 show the comparative positions for the assembly of FIG. 4;

DESCRIPTION OF THE PREFERRED EMBODIMENT

Figure 1:
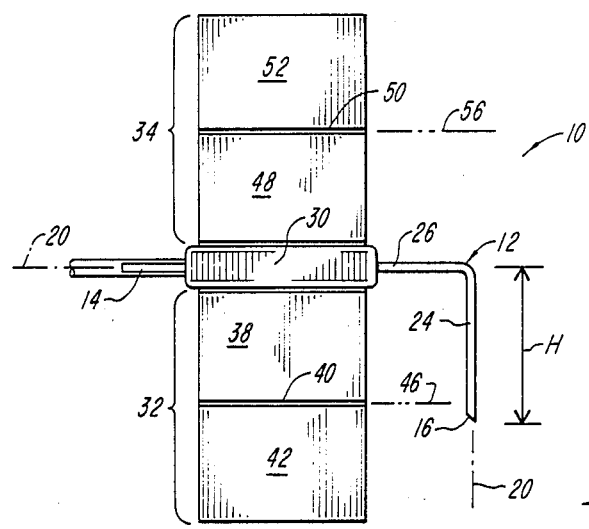
FIG. 1 shows a top view of a catheter needle assembly in accordance with the present invention.

FIG. 1 shows a top view of an exemplary catheter needle assembly 10 in accordance with the present invention. Assembly 10 includes a hollow bore needle 12 having a proximal port 14 and a distal port 16, and extending coaxially along a central needle axis 20. By way of example, the needle may be a 20 gage tubular structure made of low carbon, medical grade stainless steel, having a nominally 0.035 inch outer diameter and a nominally 0.024 inch inner diameter central bore.

The proximal port 14 is adapted for attachment to a conventional flexible catheter tube (not shown) and the distal port 16 is adapted for insertion into a patient. The needle 12 includes a distal portion 24 of length H, which includes the distal port 16 and extends along a first portion of axis 20. The needle 12 also includes a support portion 26 which extends along a linear second portion of axis 20 between the first portion of axis 20 and the proximal port 14. The portion of the needle axis 20 at the distal port 16 is angularly offset by angle A with respect to the second portion of that axis 20 which passes through the support portion 26 of needle 12. In the embodiment of FIG. 1, the angle of offset A equals ninety degrees.

As shown in FIG. 1, the first portion of axis 20 and the distal portion 24, are substantially linear. In alternate embodiments (such as that shown in FIG. 10 described below), the needle 12 may be a non-coring configuration, where the distal end of the needle (that is, the end which includes port 16) is angularly offset with respect to the remainder of portion 24, so that the peripheral edge which defines port 16 lies in a plane substantially perpendicular to the port of axis 20 passing through support portion 26. This latter form of the invention is particularly advantageous for use with an implanted access port having a self sealing silicone septum adapted for multiple penetrations by a catheter needle.

The needle assembly 10 of FIG. 1 also includes a needle support assembly which in the preferred form is made from moldable material such as PVC plastic or closed cell foams, or paper. The needle support assembly includes a coupling member 30 in the form of a hollow cylinder having an inner diameter substantially matching the outer diameter of the support portion 26 of needle 12. With this configuration, the support portion 26 of needle 12 is frictionally held within the coupling member 30. Alternatively, that support portion 26 may be cemented, or otherwise affixed, to member 30.

The needle support assembly also includes a pair of support (or wing) members 32, 34. Wing member 32 includes a first flexible sheet portion 38 which extends from the coupling member 30 and is coupled by a linear hinge portion 40 to a second flexible sheet portion 42. The hinge portion 40 extends along a first hinge axis 46.

Similarly, wing member 34 includes a first flexible sheet portion 48 which extends from the coupling member 30 and is coupled by a linear hinge portion 50 to a second flexible sheet portion 52. The hinge portion 50 extends along a second hinge axis 56. In the embodiment of FIG. 1, hinge axes 46 and 56 are parallel with the portion of axis 20 passing through support portion 20.

In the embodiment of FIG. 1, the support portion 26 of needle 12 may be rotatable about the first portion of axis 20. As shown in FIG. 1, support members 32, 34 are nominally planar, although those elements are flexible. Preferably, those members 32, 34 are attached to coupling member 30 by hinged portions permitting pivoted motion of the members 32, 34 with respect to coupling member 30 about axes parallel to the portion of axis 20 passing through support portion 26 of needle 12.

Alternatively, where the support members 32, 34 are flexible, those members may be rigidly attached to coupling member 30 so that the nominal planes of sheet portions 38 and 48 are mutually offset by an acute angle, for example, thirty degrees, although any angle may be used depending on the degree of flexibility of the sheet portions, 38 and 48.

In various embodiments, as will be discussed below, an adhesive layer may be affixed to the undersides (as shown) of sheet portions 42 and 52.

Figure 2:
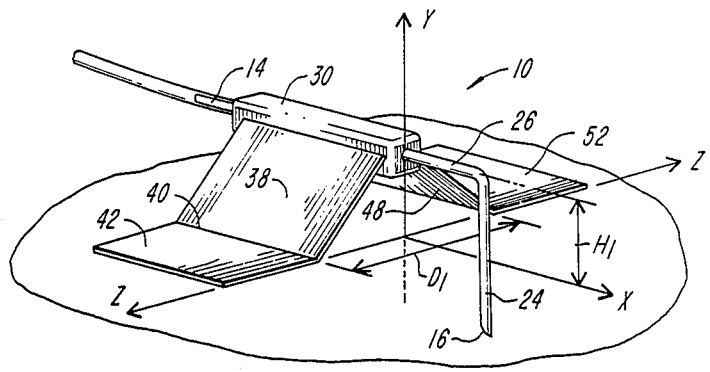
FIGS. 2 and 3 show the comparative positions for the assembly of FIG. 1.
Figure 3:
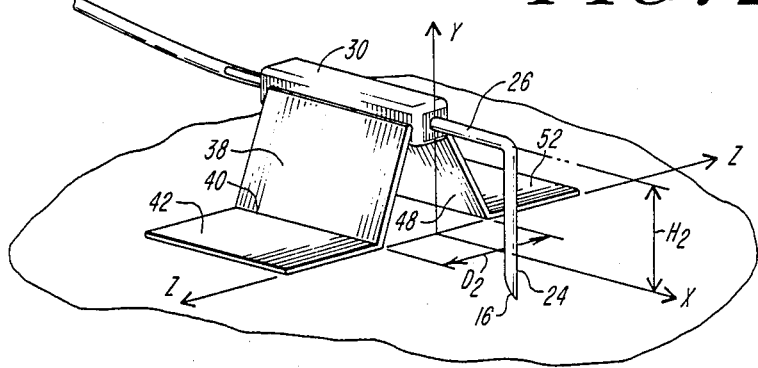

With the configuration of FIG. 1, the catheter needle assembly 10 may be used with a patient with the distal tip 16 of needle 12 inserted into the patient to a desired depth and where the needle 12 is held in place with the distal tip 16 at that depth by the needle support assembly. FIGS. 2 and 3 show two comparative positions of the catheter needle assembly 10 of FIG. 1 with respect to an XYZ coordinate system, where the XZ plane is representative of the skin of a patient.

In these respective figures, the assembly 10 is affixed to the patient's skin with the hinge axes 46 and 56 parallel and spaced apart by different predetermined distances (D1 and D2 respectively) so that the support portion 26 is positioned at correspondingly different heights above the XZ plane (which is representative of the skin surface of a patient).

As a consequence, the distal tip 16 in FIG. 2 extends below the skin surface by a distance H-H1, and the distal tip 16 in FIG. 3 extends beneath the skin surface by a distance H-H2. Thus, the embodiment of FIG. 1 may be used to support the catheter needle at adjustable heights (depending on the placement of the sheet portions 42 and 52). portions 42 and 52 may be affixed to the skin, for example, by means of tape, or by the use of an adhesive layer on the underside of portions 42 and 52.

FIGS. 4-6 show views similar to those of FIGS. 1-3 for an embodiment of the invention in which the axis 20 at distal port 16 is offset by an angle A (which is between ninety and one-hundred eighty degrees with respect to the portion of axis 20 extending through portion 26), and in which the hinge axes 46 and 56 are each offset by an offset angle O with respect the portion of axis 20 passing through portion 26. The portion of needle axis 20 passing through needle portion 24 is linear. The offset angle O is equal to the difference between needle angle A and ninety degrees. In FIGS. 4-6, element corresponding to similar elements in FIGS. 1-3, are identified by identical reference designations.

In the embodiments of the type shown in FIGS. 4-6, the position of the coupling members must be fixed axially with respect to support portion 26 of needle 12 in order to provide optimal control of the depth of penetration of distal tip 16. With this in mind for the configurations of FIGS. 4-6, the depth of penetration of distal port 16 may readily be controlled by the placement of portions 42 and 52 on the patient's skin.

The configuration of FIGS. 4-6 may also be used with a non-coring needle 12, where the distal tip of needle 12 is offset with respect to the principal part of portion 24 so that the peripheral defining edge of port 16 lies substantially in a plane parallel to that which is offset by the needle angle A portion of axis 20 passing through the portion 26.

Figure 7:
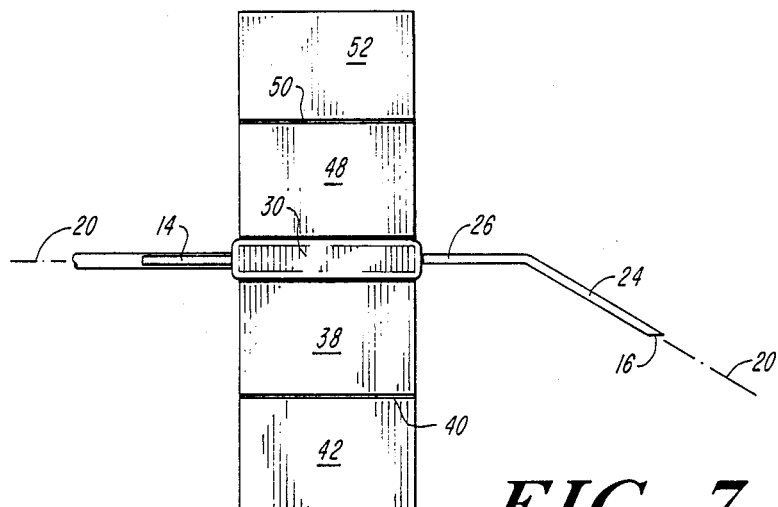
FIG. 7 shows a top view of yet another embodiment of the catheter needle assembly of the present invention.
Figure 8:
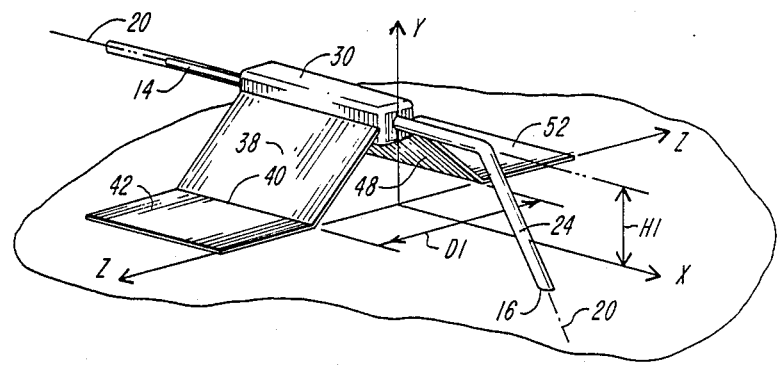
FIGS. 8 and 9 show the comparative positions for the assembly of FIG. 7.
Figure 9:
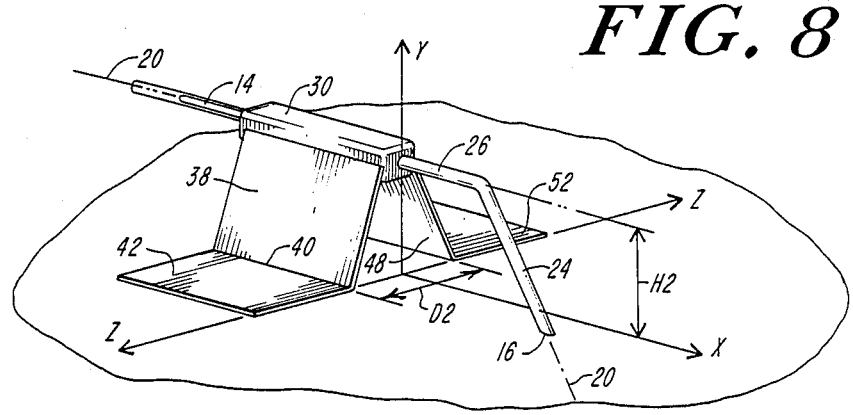

Different angle configurations (for needle 12 and hinge axis 46 and 56) may also be used in the present invention. For example, FIGS. 7-9 show views similar to FIGS. 1-3 and 4-6 for a configuration where the needle offset angle A is greater than ninety degrees and where the hinge axes 46 and 56 are parallel to the portion of axis 20 passing through support portion 26 of needle 12. In FIGS. 7-9, elements corresponding to similar elements in FIGS. 1-3, are identified by identical reference descriptions.

Figure 10:
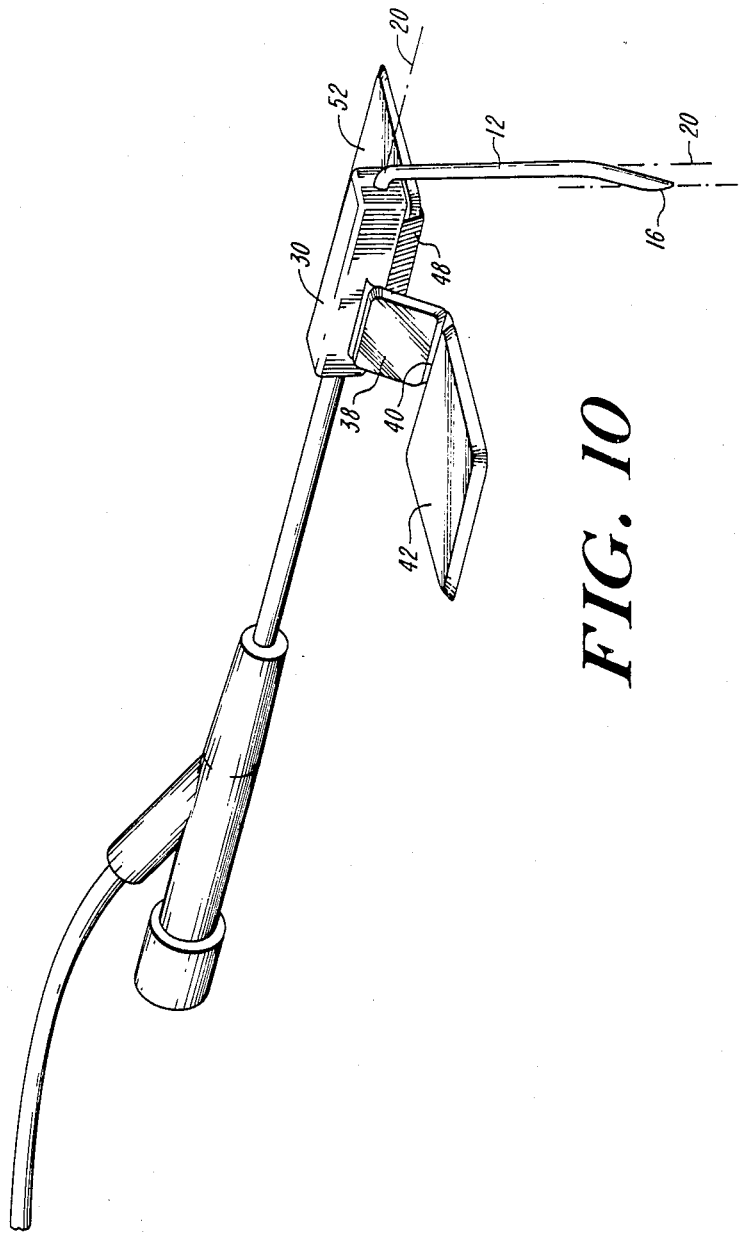
FIG. 10 shows an alternative embodiment of the present invention.

FIG. 10 shows an alternate embodiment of the invention which is similar to the embodiment of FIG. 1. In FIG. 10, elements which correspond to elements in FIG. 1 are identified with the same reference designations. In the embodiment of FIG. 10, the needle 12 has a non-coring configuration where its distal end is angularly offset with respect to the principal part of portion 24 so that the peripheral edge of needle which defines port 16 lies in a plane substantially perpendicular to the portion of axis 20 passing through the support portion 26. With this non-coring configuration, the distal tip of needle 12 may be inserted and withdrawn through the septum of an access port while minimally effecting the resealability of that septum.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A catheter needle and support assembly comprising:
    A. a hollow bore needle having a proximal port and a distal port, said needle extending along a central needle axis between said proximal port and said distal port, said needle having a distal portion including said distal port and extending along a first portion of said needle axis, and having a support portion extending along a substantially linear second portion of said needle axis between said first portion and said proximal port, wherein said needle axis at said distal port is angularly offset by a needle angle from said second portion of said needle axis,
    B. a needle support assembly including:
        i. a coupling member including means for coupling said needle support assembly to said support portion of said needle,
        ii. a pair of support members extending from said coupling member, each of said support members having a first sheet portion extending from said coupling member and coupled to a second sheet portion by a linear hinge portion extending along a hinge axis displaced from said coupling member.

2. A catheter needle and support assembly according to claim 1 wherein said first portion of said needle axis is linear and said needle angle is substantially equal to ninety degrees, and wherein said second portion of said needle axis and said hinge axes are substantially parallel.

3. A catheter needle and support assembly according to claim 2 further comprising an adhesive layer affixed to the underside of each of said second flexible sheet portions.

4. A catheter needle and support assembly according to claim 1 wherein the peripheral defining edge of said distal port lies in a reference plane, said reference plane being substantially perpendicular to said second portion of said needle axis, and wherein said second portion of said needle axis and said hinge axes are substantially parallel.

5. A catheter needle and support assembly according to claim 1 wherein each of said hinge axes are angularly offset with respect to said second portion of said needle axis by substantially the same offset angle.

6. A catheter needle and support assembly according to claim 5 wherein said first portion of said needle axis is linear and said needle angle is substantially equal to an angle between ninety degrees and one hundred eighty degrees, and wherein each of said hinge axes are offset from said second portion of said needle axis by an angle equal to the difference between said needle angle and ninety degrees.

7. A catheter needle and support assembly according to claim 6 further comprising an adhesive layer affixed to the underside of each of said second flexible sheet portions.

8. A catheter and needle assembly according to claim 4 wherein the peripheral defining edge of said distal port lies in a reference plane, said reference plane being angularly offset from said second portion of said needle axis by said needle angle.

9. A catheter needle and support assembly according to claim 1 further comprising an adhesive layer affixed to the underside of each of said second flexible sheet portions.

10. A catheter needle and support assembly according to claim 5 further comprising an adhesive layer affixed to the underside of each of said second flexible sheet portions.

11. A needle support assembly for supporting a hollow bore needle extending along a central needle axis and having a linear support portion at one end and a distal portion at the other end, wherein the needle axis at said other end is angularly offset by a needle angle from the needle axis at said support portion, comprising:
    i. a coupling member including means for coupling said needle support assembly to said support portion of said needle, whereby said needle axis at said support portion is along a reference axis,
    ii. a pair of support members extending from said coupling member, each of said support members having a first sheet portion extending from said coupling member and coupled to a second sheet portion by a linear hinge portion extending along a hinge axis displaced from said coupling member.

12. A needle support assembly according to claim 11 wherein said reference axis and said hinge axes are substantially parallel.

13. A needle support assembly according to claim 12 further comprising an adhesive layer affixed to the underside of each of said second flexible sheet portions.

14. A needle support assembly according to claim 11 wherein each of said hinge axis is angularly offset with respect to said reference axis by substantially the same offset angle.

15. A needle support assembly according to claim 11 further comprising an adhesive layer affixed to the underside of each of said second flexible sheet portions.

16. A needle support assembly according to claim 11 further comprising an adhesive layer affixed to the underside of each of said second flexible sheet portions.

* * * * *